US00PP10612P

United States Patent [19]

Nilsson

[11] Patent Number: Plant 10,612

[45] Date of Patent: Sep. 22, 1998

[54] CHRYSANTHEMUM PLANT NAMED 'PLUM CHARM'

[76] Inventor: Magnus Nilsson, AB Frillesås Handelsträdgård, Box 31, 43030 Frillesås, Sweden

[21] Appl. No.: 844,760

[22] Filed: Apr. 22, 1997

[51] Int. Cl.[6] ..... A01H 5/00

[52] U.S. Cl. ..... Plt./76

[58] Field of Search ..... Plt./76

[56] References Cited

U.S. PATENT DOCUMENTS

| | | | |
|---|---|---|---|
| P.P. 5,502 | 6/1985 | Duffett | Plt./76 |
| P.P. 7,585 | 7/1991 | VandenBerg | Plt./76 |
| 4,616,099 | 10/1986 | Sparkes | 47/58 |

OTHER PUBLICATIONS

Broertjes, et al., 1980, "A Mutant of a Mutant of a . . . Irradiation of Progressive Radiation–Induced Mutants in a Mutation Breeding Programme with *Chrysanthemum Morifolium*", Euphytica, 29:525–530.

Gosling, et al., 1979, "The Chrysanthemum Manual–6th edition", The National Chrysanthemum Society, London, Essex Telegraph Press, Ltd., pp. 329–336.

Broertjes, et al., 1978, "Application of Mutation Breeding Methods in the Improvement of Vegetatively Propagated Crops", Elsevier Sci. Pub. Co., New York, pp. 162–175.

Searle, et al., 1968, "Chrysanthemums the Year Round", Blanford Press, London, pp. 27–29, 320–327.

Chan, 1966, "Chrysanthemum and Rose Mutations Induced by x–rays", Am. Soc. Hort. Sci. Proc., pp. 613–620.

Broertjes, 1966, "Mutation Breeding of Chrysanthemums", Euphytica, 15:156–162.

Dowrick, et al., 1966, "The Induction of Mutations in Chrysanthemem Using X–and Gamma Radiation", Euphytica, 15:204–210.

*Primary Examiner*—Howard J. Locker

*Attorney, Agent, or Firm*—Foley & Lardner

[57] ABSTRACT

A Chrysanthemum plant named Plum Charm particularly characterized by its flat capitulum form; decorative capitulum type; red-purple ray floret color; diameter across face of capitulum of 101 to 121 mm when fully opened, when grown as a pinched disbudded pot mum; photoperiodic flowering response to short days of 53 to 59 days; plant height, with 14 to 16 long days after sticking unrooted cuttings and with 1 to 2 applications of 2500 ppm B-9 SP, ranges from 23 to 28 cm when grown as a pinched pot mum with 4 cuttings in a 15 cm pot; branching pattern is spreading, each plant developing 4 to 5 laterals after pinch; and recommended as a disbud pot mum.

1 Drawing Sheet

The present invention comprises a new and distinct cultivar of Chrysanthemum, botanically known as *Dendranthema grandiflora*, and referred to by the cultivar name Plum Charm.

Plum Charm, identified as 6902 (94-#02099) is a spontaneous mutation of the cultivar Dark Charm, disclosed in U.S. Plant Pat. No. 7,585, and was selected to expand the color range of the parental variety.

Plum Charm was discovered and selected by inventor Magnus Nilsson as one flowering plant within a flowering block of Dark Charm in March 1994 in a controlled environment in Frillesås, Sweden.

The first act of asexual reproduction of Plum Charm was accomplished when vegetative cuttings were taken from the initial selection in May 1994 in a controlled environment in Frillesås, Sweden, by Magnus Nilsson.

Horticultural examination of controlled flowerings of successive plantings has shown that the unique combination of characteristics as herein disclosed for Plum Charm are firmly fixed and are retained through successive generations of asexual reproduction.

Plum Charm has not been observed under all possible environmental conditions. The phenotype may vary significantly with variations in environment such as temperature, light intensity and daylength, without, however, any variance in genotype.

The following observations, measurements and comparisons describe plants grown in Salinas, Calif. and Leamington, Canada, under greenhouse conditions which approximate those generally used in commercial greenhouse practice.

The following traits have been repeatedly observed and are determined to be basic characteristics of Plum Charm, which, in combination, distinguish this Chrysanthemum as a new and distinct cultivar:

1. Flat capitulum form.
2. Decorative capitulum type.
3. Red-purple ray floret color.
4. Diameter across face of capitulum of 101 to 121 mm when fully opened, when grown as a pinched disbudded pot mum.
5. Photoperiodic flowering response to short days of 53 to 59 days.
6. Plant height, with 14 to 16 long days after sticking unrooted cuttings and with 1 to 2 applications of 2500 ppm B-9 SP, ranges from 23 to 28 cm when grown as a pinched pot mum with 4 cuttings in a 15 cm pot.
7. Branching pattern is spreading, each plant developing 4 to 5 laterals after pinch.
8. Recommended as a disbud pot mum.

The accompanying photographic drawing is a side view of a potted mum of Plum Charm, with 4 cuttings in a 15 cm pot, with the colors being as nearly true as possible with illustrations of this type.

Of the commercial cultivars known to the inventor, the most similar in comparison to Plum Charm is the parent cultivar Dark Charm. All traits of Plum Charm are similar to those of Dark Charm, except for the ray floret color. The ray floret color of Plum Charm is red-purple (R.H.S. between 63B-63C and 70B-70C), while the ray floret color of Dark Charm is described as purple-violet (R.H.S. 80B-80C, slightly overlaid with 74B).

In the following description color references are made to The Royal Horticultural Society Colour Chart. The color values were determined on plant material grown as a pinched disbudded pot mum in Salinas, Calif. on Aug. 30, 1996.

Classification:

*Botanical.*—*Dendranthema grandiflora* cv Plum Charm.

*Commercial.*—Flat decorative disbud pot mum.

Inflorescence

A. Capitulum:

*Form.*—Flat.

*Type.*—Decorative.

*Diameter across face.*—101 to 121 mm when fully opened.

Corolla of ray florets:

*Color* (*general tonality from a distance of three meters*) .—Red-purple.

*Color* (*upper surface*).—Between 63B-63C and 70B-70C).

*Color* (*under surface*).—Between 63D and 70D.

*Shape.*—Flat, straight, slightly ribbed.

C. Corolla of disc florets:

*Color* (*mature*).—154B to 154C.

*Color* (*immature*).—149B.

D. Reproductive organs:

*Androecium.*—Present on disc florets only, very few; scant pollen.

*Gynoecium.*—Present on both ray and disc florets.

Plant

A. General appearance:

*Height.*—23 to 28 cm when grown as a pinched pot mum with 14 to 16 long days after sticking unrooted cuttings prior to start of short days, with 1 to 2 applications of 2500 ppm B-9 SP.

*Branching pattern.*—Spreading, each plant developing 4 to 5 laterals after pinch.

B. Foliage:

*Color* (*upper surface*).—147A.

*Color* (*under surface*).—147B.

*Shape.*—Lobed and serrated.

What is claimed is:

1. A new and distinct Chrysanthemum plant named Plum Charm, as described and illustrated.

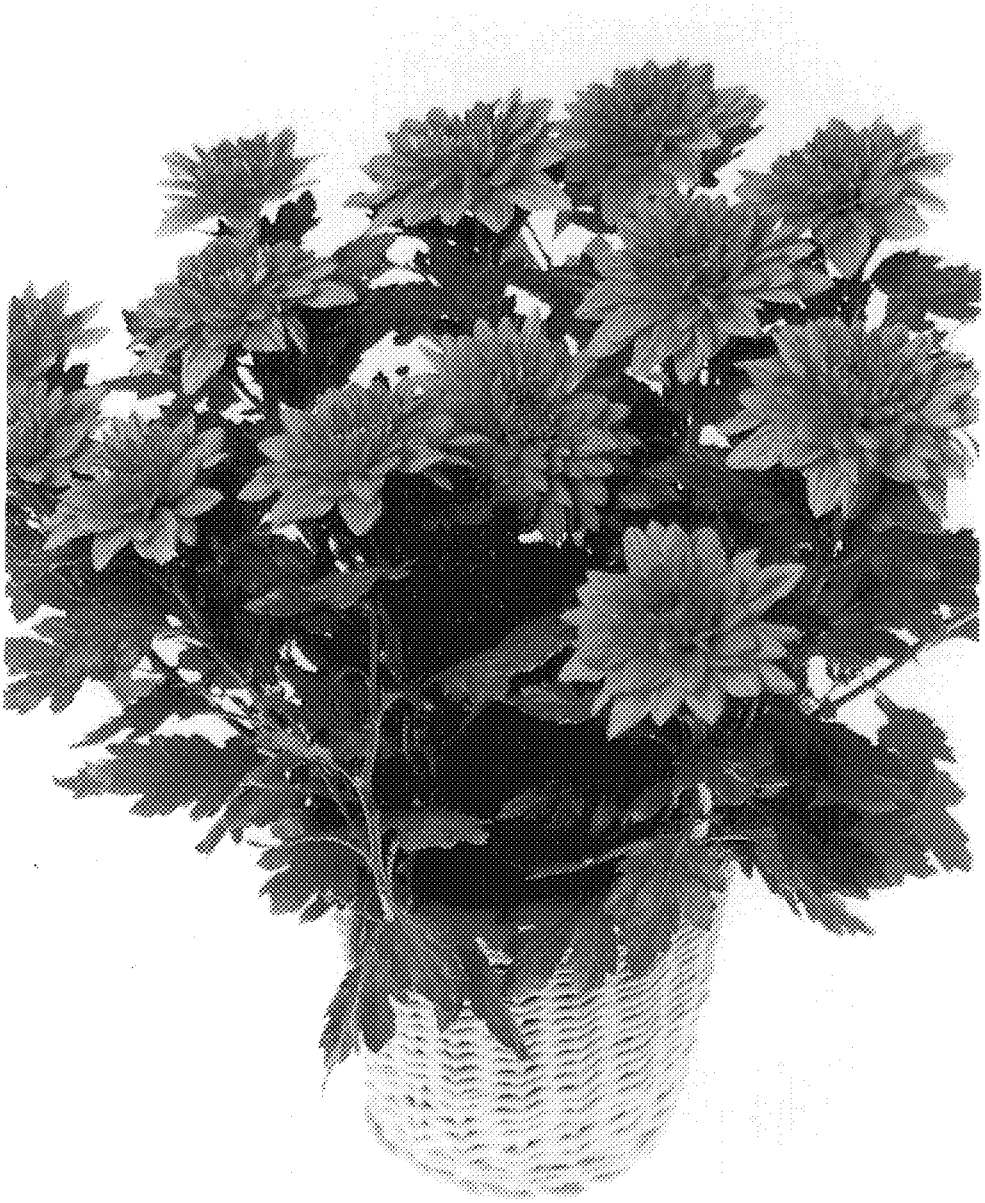

* * * * *